United States Patent [19]

Shawhan et al.

[11] Patent Number: 5,444,900

[45] Date of Patent: Aug. 29, 1995

[54] FLUID-ENCAPSULATING CASKET MATTRESS

[75] Inventors: Jim Shawhan, Centerville; Gary L. Cox, Boston, both of Ind.; Steve Woedl, Oxford, Ohio

[73] Assignee: Vandor Corporation, Richmond, Ind.

[21] Appl. No.: 53,730

[22] Filed: Apr. 27, 1993

[51] Int. Cl.⁶ .................................................. A63G 17/00
[52] U.S. Cl. ................................................. 27/19; 27/1; 27/35
[58] Field of Search ................... 27/19, 1, 35; 5/448, 5/473, 484, 487

[56] References Cited

U.S. PATENT DOCUMENTS

| | | | |
|---|---|---|---|
| 3,334,392 | 8/1967 | White | 27/19 |
| 3,576,039 | 4/1971 | Roberts | 5/484 |
| 3,691,570 | 9/1972 | Gaines et al. | 5/487 |
| 4,124,116 | 11/1978 | McCabe, Jr. | |
| 4,151,630 | 5/1979 | Havey | |
| 4,173,046 | 11/1979 | Gallagher | 5/484 |
| 4,935,022 | 6/1990 | Lash et al. | |
| 4,949,439 | 8/1990 | Semon | |
| 5,019,063 | 5/1991 | Marran et al. | |
| 5,061,259 | 10/1991 | Goldman et al. | |
| 5,092,020 | 3/1992 | McGuire | |

FOREIGN PATENT DOCUMENTS 0026542 6/1985 Japan .................................. 5/484

OTHER PUBLICATIONS

Lear of London, Absorbent Lining Advertisement in Funeral Service Journal, Jul. 1992.

*Primary Examiner*—Carl D. Friedman
*Assistant Examiner*—Beth A. Aubrey
*Attorney, Agent, or Firm*—Thompson, Hine and Flory

[57] ABSTRACT

A mattress for retaining fluids within a casket comprises:
- a liquid-impermeable elongated backing sheet;
- a liquid-permeable elongated top sheet;
- an absorbent core disposed between said backing sheet and said top sheet, the top sheet having an inner surface which is contiguous with one face of said absorbent core and said backing having an inner surface which is contiguous with the opposite face of said absorbent core, said backing sheet having a width and length greater than that of said absorbent, the backing being folded vertically upwardly at its perimeter to thereby provide side walls and end walls which form an impermeable reservoir for said fluids, said top sheet being attached to said backing sheet, said absorbent core preferably being formed from a lightweight synthetic batting.

17 Claims, 2 Drawing Sheets

FLUID-ENCAPSULATING CASKET MATTRESS

BACKGROUND OF THE INVENTION

1. Field of the Invention

This invention relates to a mattress for use in a funerary casket and more particularly to a mattress placed in a casket to absorb and retain embalming fluids and fluids accompanying the decomposition of the corpse.

2. Description of the Prior Art

The decomposition of human remains, even if embalmed, generates fluids and gases which accumulate in the casket and dissipate over time as the remains decompose. Gasketed caskets (hermetically sealed) prevent evaporation which would promote drying, permit gas pressure build up that can cause casket damage and fluid escape, and allow corrosion of the casket material by the trapped fluids and gases. The outcome of these conditions can be the escape from the casket of odorous gas and fluids. This is particularly true for above ground internment. On occasion, fluids have penetrated and escaped the bottom or sides of non-seamless caskets prior to internment.

A number of approaches have been proposed in the art to deal with the foregoing problems. For example, it is known to prepare a casket mattress having an absorbent core of highly absorbent cellulosic fibers. However, these mattresses have been found to be undesirable because they are heavy, e.g. a typical mattress may weigh 9 pounds, the fiber accumulates in local areas resulting in clumps or the fiber settles at one end of the mattress when the caskets are shipped vertically, a common practice in the trade. In addition these mattresses are bulky and when these mattresses are handled they release fibers which creates dust. Dust is a particular problem for a casket assembler who may also be painting the casket on the premises.

It is also known to place trays or pads in the bottom of a casket to prevent fluids from being released. For example, U.S. Pat. No. 4,949,439 to Semon describes a molded, one piece, high-density polyethylene drip pan which fits in the bottom of the casket for collecting and retaining the body fluids of decomposition. An absorbent pad is placed in the pan to absorb the liquids. The absorbent pad may also contain a deodorant material to mask any odors of decomposition. U.S. Pat. No. 5,092,020 to McGuire also describes a tray which is vacuum formed from recycled plastic materials. The tray has a network of interconnected upstanding ribs that create small discrete compartments for entrapment and isolation of the liquid. The compartments are designed such that the casket can be tilted at an angle of about 30° without the fluid overflowing the tray.

It is also known to line coffins with an absorbent lining one example of which is commercially available from Lear of London, Kingston Upon Thames, U.K.

It would be desirable to eliminate or greatly reduce the amount of free fluid in a casket so as to prevent accidental release of the fluid or premature failure of the casket and to do so using a casket mattress which does not suffer from the drawbacks of prior casket mattresses.

SUMMARY OF THE INVENTION

It is an object of the present invention to provide a lightweight, fluid-absorbing mattress for use in a funerary casket capable of absorbing and retaining the embalming fluids and the fluids of decomposition.

It is another object of the present invention to provide a fluid absorbing mattress for use in a burial casket which has the following advantages:

It is lightweight.

It can be compressed and shipped in bundles, yet revert to its original shape after shipping.

It is easily secured to the casket bed frame at the assembly plant for ease of shipment in a vertical attitude.

It is made from components which resist settling during vertical shipment.

It retains and gels a large volume of fluid.

It generates little or no dust during handling.

It allows the casket to be tilted over a wide angle without spilling fluid.

It is crematable.

It is economically attractive.

It is aesthetically attractive.

It provides odor control

In one embodiment of the invention, a fluid-absorbing mattress for placement in a casket comprises:

a liquid-impermeable elongated backing sheet;

a liquid-permeable elongated top sheet;

An absorbent core of a fibrous batting material disposed between said backing sheet and said top sheet;

Said top sheet having an inner surface which is contiguous with one face of said absorbent core, said backing sheet having an inner surface which is contiguous with the opposite face of said absorbent core, said backing sheet having a width and length greater than that of said absorbent core and being folded vertically upwardly at its perimeter to thereby provide side walls and end walls which form an impermeable reservoir for said fluids, said top sheet being attached to said side walls and end walls of said backing sheet so as to retain said core therein. In a preferred embodiment the absorbent core is formed from a dust-free, lightweight, crush resistant synthetic batting.

In another embodiment of the invention, the mattress contains liquid absorbing particles for improved absorption, gelling, and retention of the fluids.

In another embodiment of the invention, the liquid absorbing particles are adhered to the inner surface of the backing sheet to prevent it from accumulating in local areas of said mattress.

In yet another embodiment of the present invention, the top sheet is a porous, non-woven, synthetic web such as web formed from a spun bonded synthetic fiber.

In still another embodiment of the present invention, the top sheet is a decorative fabric such as velvet, crepe or taffeta.

DETAILED DESCRIPTION OF THE INVENTION

The present invention is described below in detail in the context of providing a fluid-absorbing and fluidencapsulating mattress for use in a funerary casket.

Figure 1:
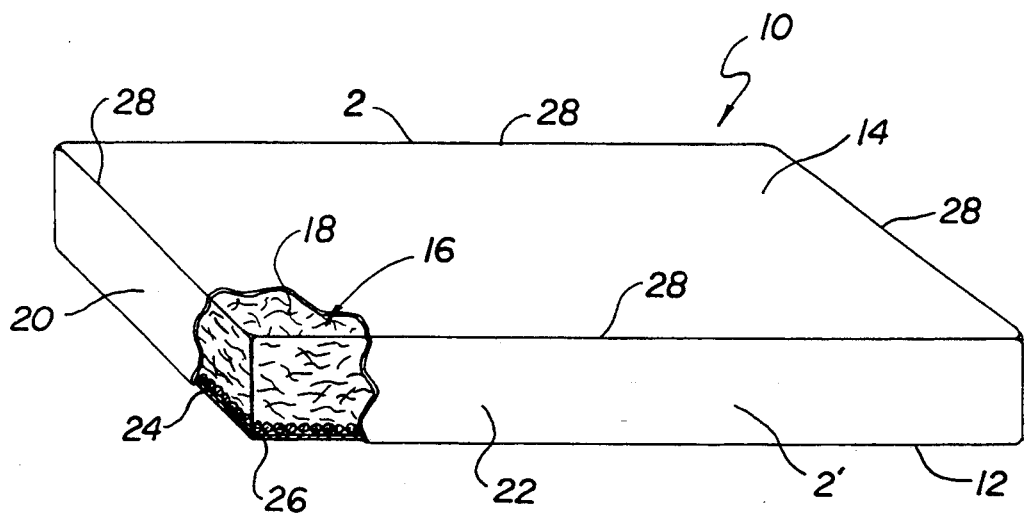
FIG. 1 is a perspective view of the mattress of the present invention with a portion of the backing sheet and the top removed to show the absorbent core and the particles of a liquid encapsulant such as a hydrogel-forming polymeric gelling agent in accordance with one embodiment of the invention.
Figure 2:
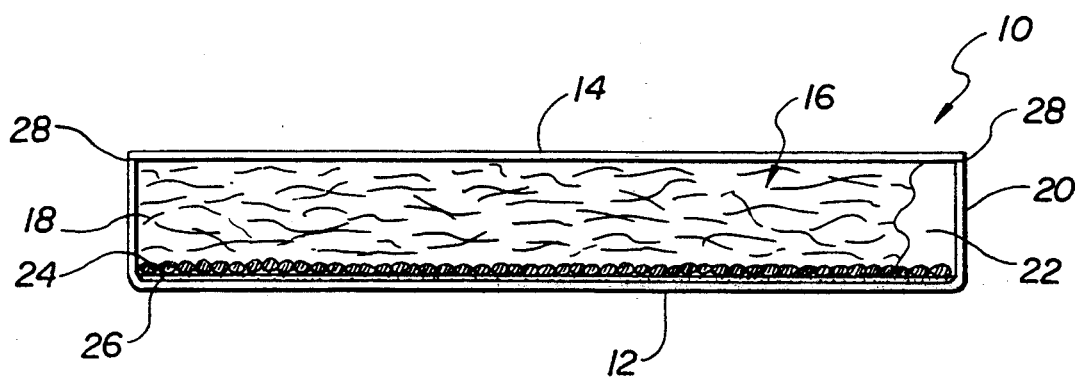
FIG. 2 is a cross-sectional side view of the mattress with a portion of the absorbent core removed to show the far side wall in accordance with the invention.

As shown in FIG. 1, the mattress 10 consists of a backing sheet 12, a top sheet 14, and an absorbent core 16. As better seen in FIG. 2, the absorbent core 16 is in the form of an open, lightweight web of interconnected fibers 18. The backing sheet 12 has a width and length greater than that of the absorbent core 16 so that the extended length and width of the backing sheet 12 can form end walls 20 and side walls 22. Walls 20 and 22 in conjunction with the backing sheet 12 form an impermeable container for the problem fluids. The peripheral edge of the top sheet is attached to the peripheral edge of the backing sheet at the upper perimeter 28 of the mattress. Attachment can be accomplished in any manner known in the art such as sewing, heat sealing or glue bonding.

In a preferred embodiment, the mattress contains discrete particles of a liquid absorbent or encapsulant such as a hydrogel-forming polymeric gelling agent 24. These particles are preferably adhered to the inner surface of the backing sheet 12 by an adhesive 26. The particles may be distributed so that they are concentrated in the head and torso portions of the mattress where the fluids typically originate.

In optional embodiments of the invention, the mattress may further contain a deodorant, a fragrance or scented material such as potpourri or any combination thereof. These materials are typically distributed on top of the core 16 under sheet 14 and/or throughout the core 16.

Figure 4:
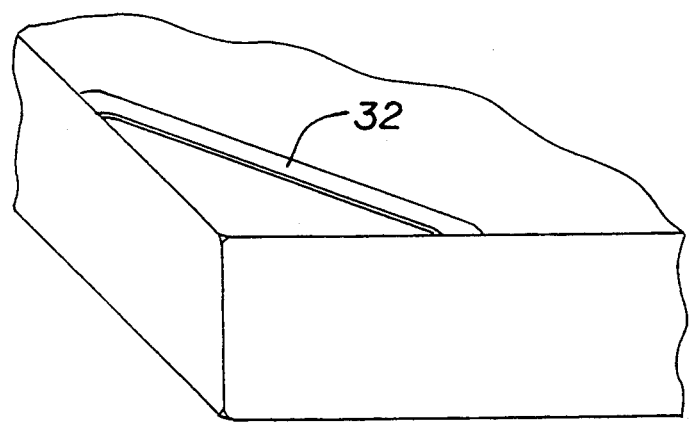
FIG. 4 is a partial perspective view of a mattress in accordance with another embodiment of the invention in which the mattress includes corner straps for securing the mattress in the casket.

In accordance with the invention, a mattress is disposed in the interior of the casket where it rests on the bed spring structure within the casket. The mattress side walls 22 and end walls 20 are juxtaposed with the casket side walls and end walls, respectively. The mattress may be constructed with diagonal corner straps 32 at the bottom corners as shown in FIG. 4 to secure the mattress on the bed of the casket so that the mattress can be shipped vertically within a casket without loss of shape.

The thickness of the mattress is not critical as long as it is thick enough to support the body and to absorb and retain sufficient fluids. Generally, the mattress should be capable of retaining a total of up to about 15 gallons of liquid and more specifically encapsulating about 5 gallons. Generally, the thickness of mattress is about 1 to 3 inches and typically it is about 2 inches.

In accordance with a preferred embodiment of the invention, the mattress contains discrete particles of a substantially water-insoluble hydrogel-forming polymeric gelling agent to improve the absorbing efficiency and fluid-containing ability of the mattress. The polymeric gelling agents are materials which, upon contact with liquids such as body fluids and embalming fluids, imbibe such liquids and form gels. In this manner, fluids discharged into the absorbent core can be acquired and encapsulated by the particles of the polymeric gelling agent, thereby providing the mattress with enhanced fluid capacity and improved fluid retention performance.

Numerous examples of useful gelling agents are known in the art. One of the most typical examples is a substantially water-insoluble, slightly cross-linked, partially neutralized hydrogel-forming polymer material disclosed in U.S. Pat. No. 4,654,039, to Brandt et al. Another example is described in U.S. Pat. No. 5,061,259 to Goldman et al. The polymeric gelling agent materials used in the absorbent core structures herein preferably have a relatively high capacity for imbibing fluids encountered in absorbent structures. The structures of the present invention will generally employ polymeric gelling agents having a gel volume of at least about 20 grams of liquid per gram of polymeric gelling agent. Polymeric absorbent particles may be employed which are commercially available. One useful material is Cyanamid Aquastor from American Cyanamid.

Sufficient absorbent is placed in the mattress to retain the amount of fluid desired. Typically, enough absorbent is placed in the mattress that the absorbent itself retains at least 2 gallons of fluid and preferably retains about 2 to 10 gallons of fluid. The mattress itself may be designed to retain a total of at least 5 gallons of fluid, i.e., fluid within the absorbent plus fluid within the mattress core and preferably a total of about 5 to 15 gallons. Using Cyanamid Aquastor absorbent polymer, about 1 to 8 ounces of polymer (dry weight) is desired.

The absorbent core of the mattress useful in this invention comprises a fiber batting material. The type of fiber is not critical and any type of fiber which is suitable for use in conventional absorbent products is also suitable for use herein. Preferably the batting is dust free, crush resistant and lightweight. A batting having a bulk density of about 6 to 10 ounces per cubic foot and typically about 8 ounces per cubic foot is particularly desirable. The batting should be crush resistant such that the mattress can be compressed for shipment and readily recover its shape when unpacked.

The fibers forming the batting may be adsorbent or absorbent, that is the fibers may retain the fluids on their surface or they may absorb the fluids internally through pores depending upon the nature of the fibers. Examples of hydrophilic fiber batting include rayon, polyesters such as polyethylene terephthalate, nylon, and like batting. Battings made from hydrophobic fiber which have been hydrophilized with a hydrophilizing agent may also be useful. Such fibers include surfactant-treated or silica-treated thermoplastic fibers derived, for example, from polyolefins such as polyethylene or polypropylene, polyacrylics, polyamides, polystyrenes, polyurethanes and the like.

A particularly preferred batting for use in the invention is polyester commercially available from Carpenter, Elkhart, Ind. This material is both lightweight and dust free. It weighs about 7 to 8 ounces per cubic foot.

The liquid impervious backing sheets can comprise any impermeable material, for example, polyolefins such as polyethylene and polypropylene, etc. which will form a fluid reservoir within the mattress. The backing material is preferably of a thickness or grade that resists puncture by sharp elements in the casket such as the capped ends of hand rail decorative fasteners and elements of the bed structure. A preferred backing is a polyethylene ranging from 1 to 10 mils thick.

The liquid pervious top sheets can comprise any woven or nonwoven material such as polyester, polyolefin, rayon and the like which is substantially porous and permits a fluid to readily pass therethrough into the underlying absorbent core structure. A breathable nonwoven fabric such as a lightweight spun bonded polypropylene which allows fluids to permeate it readily such that they can be absorbed internally is desirable to use. One example of a commercially available material is Duon from VWR Textiles. This material weighs about 2.1 ounces per square yard. Other examples are 0.085 oz. Cerex available from Monsanto and Dexter N 7601 from C. H. Dexter.

Figure 3:
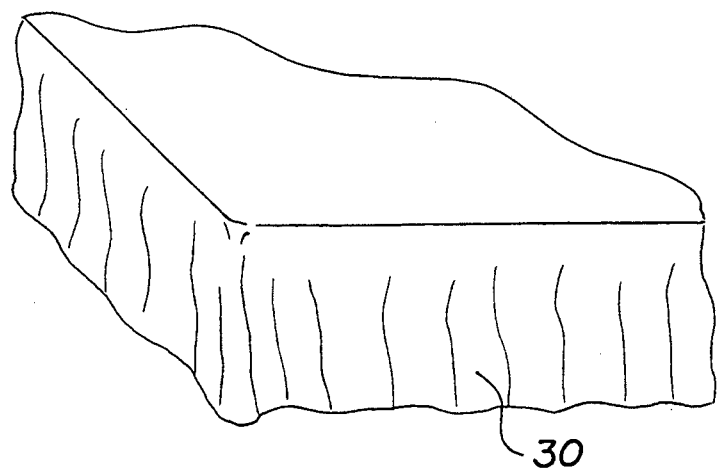
FIG. 3 is a partial perspective view of a mattress in accordance with another embodiment of the invention in which the mattress includes a skirt.

The top sheet can also be formed from any of the decorative fabrics conventionally used in casket decor such as natural or synthetic felts, velvets, taffeta and satins. The top sheet can be attached to the backing sheet by heating whereupon, if the backing is thermoplastic it will infiltrate the fabric or if the top sheet is a synthetic thermoplastic material, the fabric and the backing materials will melt together and the backing sheet and top sheet will be attached together. Alternatively, they can be sewn or adhesively bonded together. If desired, the top sheet may include a portion which extends beyond the point of attachment or seam with the backing member to form a drape 32 which decorates the sides of the mattress as shown in FIG. 3.

Having described the invention in detail and by reference to preferred embodiments thereof, it will be apparent that modifications and variations are possible without departing from the scope of the invention defined in the appended claims.

What is claimed is:

1. A mattress for retaining fluids within a casket which comprises:
    a liquid-impermeable elongated backing sheet;
    a liquid-permeable elongated top sheet; and
    an absorbent core containing a fiber batting disposed between said backing sheet and said top sheet, and particles of liquid-absorbent polymeric hydrogel in an amount sufficient to retain at least 2 gallons of fluid within said liquid-absorbent, polymeric hydrogel, said top sheet having an inner surface which is contiguous with one face of said absorbent core and said backing sheet having an inner surface which is contiguous with the opposite face of said absorbent core, said backing sheet having a width and length greater than that of said absorbent core, said backing sheet being folded vertically upwardly at its perimeter to thereby provide side walls and end walls which form an impermeable reservoir for said fluids, said top sheet being attached to the walls of said backing sheet so as to enclose said batting and said particles of said liquid-absorbent polymeric hydrogel.

2. The mattress of claim 1 wherein said absorbent core is formed from a dust-free, lightweight, crush-resistant synthetic batting.

3. The mattress of claim 2 wherein said batting is a polyester.

4. The mattress of claim 1 wherein said liquid absorbent particles are adhered to the inner surface of said backing sheet.

5. The mattress of claim 4 wherein said gelling agent is concentrated substantially in the head and torso portion of said mattress.

6. The mattress of claim 1 wherein said mattress has a thickness of about 1 to 3 inches.

7. The mattress of claim 1 including a deodorizer, a fragrant material, or any combination thereof.

8. The mattress of claim 1 wherein said backing sheet is a polyolefin film having a thickness of about 0.5 to 2.0 mils.

9. The mattress of claim 8 wherein said top sheet is a fluid permeable nonwoven fabric and said top sheet is covered with a decorative velvet or satin fabric.

10. The mattress of claim 1 wherein said top sheet is a porous, non-woven, synthetic fabric.

11. The mattress of claim 1 wherein said top sheet is a decorative felt, velvet or satin fabric.

12. The mattress of claim 1 wherein said mattress includes means for securing said mattress within the casket such that said mattress can be shipped vertically within a casket without loss of shape.

13. The mattress of claim 12 wherein said means for securing said mattress within the casket include diagonal corner straps.

14. The mattress of claim 1 wherein said top sheet includes peripheral extending portions which drape over the side walls of said mattress.

15. The mattress of claim 1 wherein said mattress can be compressed for shipment and readily recovers its shape upon being unpackaged.

16. The mattress of claim 1 wherein said liquid-permeable elongated top sheet is a breathable, woven or non-woven fabric which permits a fluid to readily pass therethrough.

17. A mattress for retaining fluids within a casket which comprises:
    a liquid-impermeable elongated backing sheet;
    a liquid-permeable elongated top sheet; and
    an absorbent core containing a fiber batting disposed between said backing sheet and said top sheet, and particles of a liquid-absorbent polymeric hydrogel in an amount sufficient to retain at least 2 gallons of fluid within said liquid-absorbent polymeric hydrogel, said top sheet having an inner surface which is contiguous with one face of said absorbent core and said backing having an inner surface which is contiguous with the opposite face of said absorbent core, said backing sheet having a width and length greater than that of said absorbent core, said backing sheet being folded vertically upwardly at its perimeter to thereby provide side walls and end walls which form an impermeable reservoir for said fluids, said top sheet being attached to the walls of said backing sheet so as to enclose said batting and said particles of said liquid-absorbent polymeric hydrogel, wherein said particles of said liquid-absorbent polymeric hydrogel are concentrated substantially in the head and torso portion of said mattress and adhered to the inner surface of said backing sheet, said mattress having a thickness of about 1 to 3 inches and a total fluid capacity of about 5 to 10 gallons; said mattress further comprising diagonal corner strap means for securing said mattress within said casket.

* * * * *